(12) United States Patent
Suzuki et al.

(10) Patent No.: US 7,652,025 B2
(45) Date of Patent: Jan. 26, 2010

(54) REMEDIES FOR SEPSIS

(75) Inventors: Tomohiko Suzuki, Kamakura (JP);
Hideaki Inada, Kamakura (JP);
Yoshitaka Yoshizawa, Kamakura (JP);
Kuniaki Kawamura, Kamakura (JP);
Toshiaki Tanaka, Zushi (JP)

(73) Assignee: Toray Industries, Inc. (JP)

( * ) Notice: Subject to any disclaimer, the term of this patent is extended or adjusted under 35 U.S.C. 154(b) by 201 days.

(21) Appl. No.: 10/477,062

(22) PCT Filed: May 8, 2002

(86) PCT No.: PCT/JP02/04469

§ 371 (c)(1),
(2), (4) Date: Dec. 18, 2003

(87) PCT Pub. No.: WO02/089845

PCT Pub. Date: Nov. 14, 2002

(65) Prior Publication Data

US 2004/0147536 A1 Jul. 29, 2004

(30) Foreign Application Priority Data

May 8, 2001 (JP) ............................. 2001-137737

(51) Int. Cl.
*A01N 43/42* (2006.01)
*A61K 31/44* (2006.01)
(52) U.S. Cl. ...................... 514/281; 514/280
(58) Field of Classification Search ............... 514/281, 514/291, 273, 280
See application file for complete search history.

(56) References Cited

U.S. PATENT DOCUMENTS 5,420,154 A * 5/1995 Christensen et al. ........ 514/424
6,608,105 B2 * 8/2003 Asakawa et al. ............ 514/460

FOREIGN PATENT DOCUMENTS

| EP | 1275388 | * | 1/2003 |
| JP | 11-60483 | A | 3/1999 |
| JP | 11-60484 | A | 3/1999 |
| WO | WO 92/21340 | * | 12/1992 |
| WO | 9924471 | | 5/1999 |
| WO | 9959997 | | 11/1999 |

OTHER PUBLICATIONS

Nagase et al. (Chem Pharm Bull (Tokyo), Feb. 1998, 46(2):366-9.*
Alicea et al. (J NeuroImmunology, Jan. 1996, 64, 1, 83-90).*
Lauzurica et al. (Eur J of Immunol. 1999, 29, 1890-99).*
Mira et al. (Jama, 282, 6, 11, 1999).*
James M. Harkema et al., "Pharmacologic Agents in the Treatment of Ischemia. Hemorrhagic Shock and Sepsis", 1992, vol. 7., No. 3, pp. 182-216, *Journal of Critical Care*.
Joseph Mamazza et al., "The Pulmonary Effects of Opiate Blockade in Septic Shock", 1984, vol. 36, pp. 625-630, *Journal of Surgical Research*.
James M. Chamberlain et al. "A Comprehensive Review of Naloxone for the Emergency Physician", 1994, vol. 12, No. 6, pp. 650-660, *American Journal of Emergency Medicine*.
Oscar Arrieta et al., "Pharmacological Treatment of Septic Shock", 2000, vol. 10, No. 5, pp. 601-621, *Expert Opinion on Therapeutic Patents*.

* cited by examiner

*Primary Examiner*—Sreeni Padmanabhan
*Assistant Examiner*—Umamaheswari Ramachandran
(74) *Attorney, Agent, or Firm*—DLA Piper LLP (US)

(57) ABSTRACT

A therapeutic agent for sepsis and various symptoms accompanying sepsis (such as septic shock, disseminated intravascular coagulation syndrome, adult respiratory distress syndrome and multiple organ dysfunction) is disclosed. The therapeutic agent for sepsis according to the present invention comprises as an effective ingredient an opioid κ receptor agonist compound such as (−)-17-(cyclopropylmethyl)-3, 14β-dihydroxy-4,5α-epoxy-6β[N-methyl-trans-3-(3-furyl) acrylamide] oxide derivative. The opioid κ receptor agonist compound may be administered as it is or in the form of a pharmaceutical composition prepared by mixing the compound with a known pharmaceutically acceptable acid, carrier or vehicle orally or parenterally.

2 Claims, 1 Drawing Sheet

Fig. 1

REMEDIES FOR SEPSIS

TECHNICAL FIELD

The present invention relates to a novel therapeutic agent for sepsis containing an opioid κ receptor agonist.

BACKGROUND ART

Sepsis is a severe systemic infectious disease in which bacteria continuously or intermittently enter the blood from an infection focus, which is caused by diseases such as infectious diseases, cirrhosis, renal failure, diabetes and dystocia, or by therapies against injury or disease, such as indwelling catheter, transfusion device, dialysis or tracheostomy. In its broader sense, sepsis is not restricted to the invasion by a microorganism into a host, but is defined to include clinical conditions of infectious diseases, in which two or more of the following are met: (1) body temperature >38° C. or <36° C.; (2) heart rate >90 beats/min.; (3) frequency of respiration >20 breaths/min. or $PaCO_2$<32 mmHg; (4) number of leukocytes >12,000/μl or <4000/μl, or ratio of stab neutrophil>10%. Recently, the pathological conditions exhibiting these symptoms are called systemic inflammatory response syndrome (SIRS) (Crit. Care Med., 20:864-874, 1992). Sepsis further includes organ dysfunction, severe sepsis complicated with hypoperfusion or hypotension, lactic acidosis, hypouresis and septic shock complicated with consciousness disorder (Chest,101:1644-1655,1992). Severe sepsis and septic shock induce disseminated intravascular coagulation syndrome (DIC), adult respiratory distress syndrome (ARDS) and multiple organ dysfunction (MODS).

The causative bacteria of sepsis are mainly *staphylococci, streptococci, Escherichia coli, Pseudomonas aeruginosa, Klebsiella and Enterobacter*. By the infection of these bacteria, high fever, chill, tachycardia and strong systemic symptoms are exhibited, and existence of the infective bacteria is often confirmed in the arterial blood, venous blood, spinal fluid and bone marrow fluid.

Recently, due to the development of various strong antibiotics, sepsis caused by these bacteria is decreasing. However, sepsis caused by new bacteria such as MRSA, which acquired a resistant gene is increasing. Reflecting the increase of treatments using indwelling catheter or transfusion device, dialysis, and invasive treatments and surgery such as tracheostomy, there is a tendency that the larger the scale of the hospital, the more the occurrence of sepsis. Further, frequency of sepsis is increasing among those having poor resistance to infections, such as newborns, elder people, patients suffering from hematopoietic organ tumors and patients whose immunities are decreased due to administration of adenocorticotropic hormones or anticancer agents. Thus, sepsis is continuously increasing in spite of the development of medicine.

A method for prevention or therapy of sepsis now employed is carried out by administering the best antibiotic against the causative bacterium after detecting the causative bacterium and determining the sensitivities thereof to antibiotics, and by simultaneously promoting the defending ability of the host by fluid replacement, replenishment of electrolytes, improvement of hypoproteinemia, replenishment of nutrients, administration of γ-globulin and the like (Masataka KATSU, Encyclopedia of medical sciences,37:263-265, 1984). In cases where the shock unfortunately appears, treatments such as removal of lesion by surgery, improvement of circulatory dysfunction, administration of opsonin-activating substances, administration of adenocorticotropic hormones, administration of synthetic protease inhibitors, and the like are carried out. However, since the symptoms of the underlying basal disease and the symptoms of sepsis overlap, clear diagnosis is not easily carried out, which often gives difficulty in the prevention and therapy of sepsis. In cases where the septic shock occurs, the prevention and therapy are difficult. Thus, sepsis is a disease which gives a high death rate even at present.

The death rate of sepsis varies from 10%-20% s to 50% depending on the report. Forty percent of sepsis cases are complicated with septic shock, and the prognosis of the shock is bad. There is a report which shows the death rate of the shock is 77 to 90% (New Development of Sepsis, pp3-8, Medicine Journal Co., Ltd., 1998, Ann Intern Med 115: 457-469, 1991). Therefore, the primary object of the therapy is the prevention of the septic shock. If the changes which occurs in the initial stage of the shock are grasped and early diagnosis is attained, early treatment can be attained and improvement of prognosis is expected. However, although a number of anti-shock drugs and therapeutic methods have been studied, almost none of them were judged effective.

It is thought that sepsis is caused by inflammatory cytokines such as tumor necrosis factor (TNF), interleukin 1 (IL-1), interleukin 6 (IL-6) and interleukin 8 (IL-8), which are excessively produced by monocytes, macrophages, vascular endothelial cells and the like in response to the infectious stimuli (such as bacterial cells per se, endotoxins, cell wall components which are peptide glycan/teichoic acid complexes and exotoxins). By the excessively produced inflammatory cytokines, eicosanoid and lipid mediators of platelet-activating factor are released, and the cytokine net work is activated by the interaction thereof, so that the inflammatory reaction is amplified. During this process, complement system, coagulation system, kinin system and adrenocorticotropic hormone/endorphin system are also activated, and the systemic inflammatory reaction of which underlying symptom is vascular endothelial disorder is induced. For expression of circulatory disorders or histotoxic disorders, participation of elastase originated from granulocytes and active oxygen has been shown (New Development of Sepsis, pp3-8, Medicine Journal Co., Ltd., 1998).

Therefore, a number of clinical tests of the therapeutic methods which inhibit the inflammatory cytokines, represented by administration of substances that inhibit the inflammatory cytokines have been carried out. However, all of them were unsuccessful (Lancet,351:929-933,1998, JAMA,271: 1836-1843,1994). Bone suggested that the reason for the failure of the tests may be the homeostasis in the body by which an action in the body necessarily accompanies a counteraction therefor so that they are balanced (Crit. Care Med., 24:1125-1128,1996). In fact, it is known that surgery or severe acute pancreatitis induces both the inflammatory cytokines and the anti-inflammatory cytokines or inflammatory cytokine-inhibiting substances (Intensive Care, 10;815-822,1998). If the induction of the anti-inflammatory cytokines is too strong, anergy is presented or the patient becomes easily infective. This anti-inflammatory cytokines-dominant state is called compensatory anti-inflammatory response syndrome (CARS), and participates in the onset of organ dysfunction in sepsis together with SIRS. That is, the pathological state of sepsis is double-faced, and it is important for the therapy to control both the inflammatory cytokine reactions and the anti-inflammatory cytokine reactions. Therefore, it is thought that therapeutic effects of the therapies in which only one of the reactions is inhibited by inhibition of inflammatory cytokines or the like were not exhibited.

Although intensive care developed during this 20 years, the death rate of sepsis is kept high and there are substantially no effective remedies. The reason therefor is that the pathological conditions of sepsis have not yet been completely understood (Nath. J. Med.,55:132-141,1999). It is also a reason therefor that therapeutic effects of drugs were studied by administering the test drugs before inducing the experimental sepsis in non-clinical animal tests.

Opioid drugs represented by morphine are widely used clinically as analgesics. It is thought that an opioid binds to an opioid receptor existing on the cell membrane and changes ion channels or enzymes through G protein, thereby exhibiting its pharmacological effectsThere are three types of opioid receptors called δ, κ and μ, and structures of these receptors were clarified by the cloning of the genes (Pharmacol. Rev., 48:567-592,1996). Most of the opioids clinically used are the drugs which act on μ receptor. Known agonists include morphine, codeine, oxycodone, pethidine and fentanyl, and known antagonists include naloxone and levallorphan. Other clinically used opioids include butorphanol, pentazocine and eptazocine, and they act on both μ receptor and κ receptors (Basis and Clinic of Opioids, pp9-15, MIX Co., Ltd., 2000). Known pharmacological actions of the compounds which act on μ receptor include actions causing analgesia, miosis, respiratory depression, emesis or nausea, constipation, euphoria and pruritus.

As for the compounds which selectively act on κ receptor, no drugs which can be clinically used have been obtained. However, a number of compounds which can be non-clinically used are known, and clinical tests of some of them are now being conducted (Exp. Opin. Invest. Drugs,6:1351-1368,1997). Known pharmacological actions of the compounds which act on κ receptor include actions causing analgesia, sedation, discomfort, diuresis, cell protection and antipruritus.

As for the actions of opioids on sepsis, the action of morphine which is a μ agonist, and the action of naloxone which is a μ antagonist, are reported. The former is reported to decrease survival rate of experimental sepsis models, and the latter, naloxone, is reported to suppresses fever of experimental sepsis models (J. Neuroimmuneol.,95:107-114,1999, Eur. J. Pharmacol.,401:161-165,2000). U.S. Pat. Nos. 4,267,182 (1981) and 4,434,168 (1984) describe narcotic antagonists for therapies of various shocks. However, compounds which selectively act on κ receptor are not described. It is not clear how a compound which acts on κ receptor behaves with respect to sepsis.

On the other hand, U.S. Pat. No. 5,482,930 (1996) discloses anti-inflammation actions of des-Tyr dynorphine which is one of the compounds that act on κ receptor and of analogues thereof.

DISCLOSURE OF THE INVENTION

An object of the present invention is to provide a therapeutic agent for sepsis and various symptoms accompanying sepsis (such as septic shock, disseminated intravascular coagulation syndrome, adult respiratory distress syndrome and multiple organ dysfunction).

As a result of intensive study by the present inventors for overcoming the above-described problem, the present inventors discovered that opioid κ agonist compounds serve as therapeutic agents for sepsis and various symptoms accompanying sepsis, thereby completing the present invention.

That is, the present invention provides a therapeutic agent for sepsis comprising an opioid κ receptor agonist compound as an effective ingredient. The term "opioid κ receptor agonist compound" means a compound which has selectivity to κ receptor irrespective of the chemical structural specificity. Particularly, the compounds described in Japanese Patent No. 2525552, WO98/23290, U.S. Pat. No. 4,145,435 (1979), U.S. Pat. No. 4,360,531 (1982), U.S. Pat. No. 4,359,476 (1982), EP Patent No. 108602 (1983), U.S. Pat. No. 4,855,316 (1989), European Patent No. 372466 (1989), European Patent No. 393696 (1990), U.S. Pat. No. 4,906,655 (1990), U.S. Pat. No. 4,438,130 (1984), U.S. Pat. No. 4,663,343 (1987), U.S. Pat. No. 5,760,023 (1998), Japanese Laid-open PCT Application No. 11-512075 (1999) and so on. More particularly, the present invention provides:

a therapeutic agent for sepsis comprising, as an effective ingredient, an opioid κ receptor agonist compound which is a morphinan derivative represented by the following Formula (I):

(I)

[wherein ----- represents a double bond or single bond; $R^1$ represents $C_1$-$C_5$ alkyl, $C_4$-$C_7$ cycloalkylalkyl, $C_5$-$C_7$ cycloalkenylalkyl, $C_6$-$C_{12}$ aryl, $C_7$-$C_{13}$ aralkyl, $C_4$-$C_7$ alkenyl, allyl, $C_1$-$C_5$ furan-2-ylalkyl or $C_1$-$C_5$ thiophene-2-ylalkyl; $R_2$ represents hydrogen, hydroxy, nitro, $C_1$-$C_5$ alkanoyloxy, $C_1$-$C_5$ alkoxy, $C_1$-$C_5$ alkyl or —$NR^9R^{10}$ wherein $R^9$ represents hydrogen or $C_1$-$C_5$ alkyl and $R^{10}$ represents hydrogen or $C_1$-$C_5$ alkyl or —C(=O)$R^{11}$ wherein $R^{11}$ represents hydrogen, phenyl or $C_1$-$C_5$ alkyl; $R^3$ represents hydrogen, hydroxy, $C_1$-$C_5$ alkanoyloxy or $C_1$-$C_5$ alkoxy; A represents —XC(=Y)—, —XC(=Y)Z-, —X— or —$XSO_2$— (wherein X, Y and Z independently represent $NR^4$,S or O wherein $R^4$ represents hydrogen, $C_1$-$C_5$ linear or branched alkyl or $C_6$-$C_{12}$ aryl, $R^4$s in the formula may be the same or different); B represents valence bond, $C_1$-$C_{14}$ linear or branched alkylene (with the proviso that said alkylene may have at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl and phenoxy, and that 1 to 3 methylene groups in said alkylene may be substituted with carbonyl group(s)), $C_2$-$C_{14}$ linear or branched acyclic unsaturated hydrocarbon containing 1 to 3 double bonds and/or triple bonds (with the proviso that said acyclic unsaturated hydrocarbon may have at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl and phenoxy, and that 1 to 3 methylene groups in said acyclic unsaturated hydrocarbon may be substituted with carbonyl group(s)), or $C_1$-$C_{14}$ linear or branched saturated or unsaturated hydrocarbon containing 1 to 5 thioether bonds, ether bonds and/or amino bonds (with the proviso that a hetero atom does not directly binds to A, and that 1 to 3 methylene groups in said acyclic unsaturated hydrocarbon may be substituted with carbonyl group(s)); $R^5$ represents hydrogen or an organic group having a skeleton selected from those shown below

Q: NH, O, S

T: $CH_2$, NH, S, O
l = 0–5
m, n ≥ 0
m + n ≤ 5

(wherein Q represents NH, O or S; T represents $CH_2$, NH, S or O; l represents an integer of 0 to 5; and m and n independently represent integers of not less than 0, the total of m and n being not more than 5; each of said organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy);

$R^6$ represents hydrogen; $R^7$ represents hydrogen, hydroxy, $C_1$-$C_5$ alkoxy or $C_1$-$C_5$ alkanoyloxy; or $R^6$ and $R^7$ cooperatively represent —O—, —$CH_2$— or —S—; and $R^8$ represents hydrogen, $C_1$-$C_5$ alkyl or $C_1$-$C_5$ alkanoyl]

or a pharmaceutically acceptable acid addition salt thereof;

a therapeutic agent for sepsis comprising, as an effective ingredient, an opioid κ receptor agonist compound which is a morphinan quaternary ammonium salt derivative represented by the following Formula (II):

(II)

[wherein ----- represents a double bond or single bond; $R^1$ represents $C_1$-$C_5$ alkyl, $C_4$-$C_7$ cycloalkylalkyl, $C_5$-$C_7$ cycloalkenylalkyl, $C_7$-$C_{13}$ aralkyl, $C_4$-$C_7$ alkenyl or allyl; $R^2$ represents hydrogen, hydroxy, nitro, $C_1$-$C_5$ alkanoyloxy, $C_1$-$C_5$ alkoxy or $C_1$-$C_5$ alkyl; $R^3$ represents hydrogen, hydroxy, $C_1$-$C_5$ alkanoyloxy or $C_1$-$C_5$ alkoxy; $R^4$ represents hydrogen, $C_1$-$C_5$ linear or branched alkyl or $C_6$-$C_{12}$ aryl; A represents $C_1$-$C_6$ alkylene, —CH=CH— or —C≡C—; $R^5$ represents hydrogen or an organic group having a skeleton selected from those shown below

Q: O, S

T: $CH_2$, NH, S, O
l = 0–5
m, n ≥ 0
m + n ≤ 5

(wherein Q represents O or S; T represents $CH_2$, NH, S or O; l represents an integer of 0 to 5; and m and n independently represent integers of not less than 0, the total of m and n being not more than 5; each of said organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, nitro, cyano, isothiocyanato, trifluoromethyl, trifluoromethoxy and methylenedioxy);

$R_6$ represents $C_1$-$C_5$ alkyl or allyl; and X represents a pharmaceutically acceptable counter ion];

a therapeutic agent for sepsis comprising, as an effective ingredient, an opioid κ receptor agonist compound which is a oxide-N-oxide derivative represented by the following Formula (III):

(III)

[wherein ----- represents a double bond or single bond; $R^1$ represents $C_1$-$C_5$ alkyl, $C_4$-$C_7$ cycloalkylalkyl, $C_5$-$C_7$ cycloalkenylalkyl, $C_6$-$C_{12}$ aryl, $C_7$-$C_{13}$ aralkyl, $C_4$-$C_7$ alkenyl or allyl; $R^2$ represents hydrogen, hydroxy, nitro, $C_1$-$C_5$ alkanoyloxy, $C_1$-$C_5$ alkoxy or $C_1$-$C_5$ alkyl; $R^3$ represents hydrogen, hydroxy, $C_1$-$C_5$ alkanoyloxy or $C_1$-$C_5$ alkoxy; $R^4$ represents hydrogen, $C_1$-$C_5$ linear or branched alkyl or $C_6$-$C_{12}$ aryl; A represents $C_1$-$C_6$ alkylene, —CH=CH— or —C≡C—; $R^5$ represents hydrogen or an organic group having a skeleton selected from those shown below (wherein T represents $CH_2$ or O; l represents an integer of 0 to 5; and m and n independently represent integers of not less than 0, the total of m and n being not more than 5; each of said organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, nitro, cyano, isothiocyanato, trifluoromethyl, trifluoromethoxy and methylenedioxy)]

or a pharmaceutically acceptable acid addition salt thereof;

a therapeutic agent for sepsis comprising, as an effective ingredient, an opioid κ receptor agonist compound which is a compound represented by the following Formula (IV):

(IV)

[wherein the wavy lines (~) between the cyclohexane ring and the two nitrogen atoms represent bonds which are cis or trans with respect to the cyclohexane ring; A represents valence bond, —$(CH_2)_q$—, —$CH(CH_3)$— or —X$(CH_2)_n$— (wherein q represents an integer of 1 to 4; n represents an integer of 1 to 4; and X represents O or S); Ar represents a carbocyclic aromatic ring, heterocyclic aromatic ring, bicarbocyclic aromatic ring, tricarbocyclic aromatic ring or diphenylmethyl, each of said carbocyclic aromatic ring, heterocyclic aromatic ring, bicarbocyclic aromatic ring, tricarbocyclic aromatic ring and diphenylmethyl may have one or more substituents selected from the group consisting of hydrogen, halogen, trifluoromethyl, nitro, $C_1$-$C_3$ alkoxy, hydroxy, azide, $C_1$-$C_3$ alkyl, methanesulfonyl, cyano, amino, $C_1$-$C_3$ alkoxycarbonyl, $C_1$-$C_3$ alkanoyloxy and $C_1$-$C_3$ acylamino represented by —NHC(=O)$R_7$ (wherein $R_7$ represents hydrogen or $C_1$-$C_2$ alkyl); R represents hydrogen, $C_1$-$C_3$ alkyl or allyl; $R^1$ and $R^2$ independently represent hydrogen, $C_1$-$C_3$ alkyl or allyl, or $R^1$, $R^2$ and the nitrogen atom to which they bind cooperatively represent azetidinyl, pyrrolidinyl, 3-hydroxypyrrolidinyl, 3-fluoropyrrolidinyl, morpholinyl, piperidinyl or 3,4-dehydropiperidinyl; $R^3$, $R^4$, $R_5$ and $R_6$ independently represent hydrogen, hydroxy, $OR^8$ or OC(=O)$R_9$, or $R^5$ and $R^6$ cooperatively represent -E-$CH_2$—$CH_2$-E-, =E, —$CH_2$—$CH_2$—$CH_2$-Z- or —$CH_2$—$CH_2$-Z-$CH_2$— (wherein Z represents oxygen (—O—), —$NR^{10}$—, sulfur (—S—), —S(=O)— or —S(=O)$_2$—; E represents N—OH, N—OC(=O)$CH_3$, oxygen or sulfur; $R^8$ represents $C_1$-$C_3$ alkyl; and $R^9$ represents hydrogen or $C_1$-$C_3$ alkyl]

or a pharmaceutically acceptable acid addition salt thereof; and a therapeutic agent for sepsis comprising, as an effective ingredient, an opioid κ receptor agonist compound which is a compound represented by the following Formula (V):

(D)Phe-R1-R2-R3-Q  (V)

[wherein R1 represents (D)NapAla or (D)Phe; R2 represents (D)Nle, Trp or (D)Ile; R3 represents (D)Arg or (D)ChAla; Q is a C-terminal structure of the peptide and represents —(C=O)OH or —(C=O)NXY (wherein X represents hydrogen or $C_1$-$C_6$ alkyl; and Y represents hydrogen or $C_1$-$C_6$ alkyl)]

or a pharmaceutically acceptable acid addition salt thereof.

In the present specification, the term "organic group having a skeleton" in Formulae (I), (II), (III) and so on means the monovalent group formed by elimination of one hydrogen atom from the ring constituting each of the compounds shown as skeletons, and the monovalent group just mentioned above having at least one substituent described above. In the present specification, the following abbreviations are used for designating amino acid residues:

TABLE 1

| Amino Acid | Abbreviation |
| --- | --- |
| alanine | Ala |
| arginine | Arg |
| cyclohexylalanine | ChAla |
| isoleucine | Ile |
| naphthylalanine | NapAla |
| norleucine | Nle |
| phenylalanine | Phe |
| tryptophan | Trp |

Amino acids are designated as described above by the well-known codes. "(D)" indicates amino acids having D-configuration in contrast to the naturally occurring L-amino acids. The amino acids of which configurations are not indicated are (L)-amino acids.

The present invention also provides use of the opioid κ receptor agonist compound for the production of a therapeutic agent for sepsis. The present invention further provides a therapeutic method for sepsis comprising administering the opioid κ receptor agonist compound to a patient suffering from sepsis.

BEST MODE FOR CARRYING OUT THE INVENTION

As mentioned above, the present invention provides a therapeutic agent for sepsis comprising an opioid κ receptor agonist compound as an effective ingredient. The term "opioid κ receptor agonist compound" means a compound which has selectivity to κ receptor irrespective of the chemical structural specificity. Particularly, the compounds described in Japanese Patent No. 2525552, WO98/23290, U.S. Pat. No. 4,145,435 (1979), U.S. Pat. No. 4,360,531 (1982), U.S. Pat. No. 4,359,476 (1982), EP Patent No. 108602 (1983), U.S. Pat. No. 4,855,316 (1989), European Patent No. 372466 (1989), European Patent No. 393696 (1990), U.S. Pat. No. 4,906,655 (1990), U.S. Pat. No. 4,438,130 (1984), U.S. Pat. No. 4,663,343 (1987), U.S. Pat. No.

5,760,023 (1998), Japanese Laid-open PCT Application No. 11-512075 (1999) and so on. More particularly, the present invention provides: a therapeutic agent for sepsis comprising, as an effective ingredient, an opioid κ receptor agonist compound which is a morphinan derivative represented by the following Formula (I):

(I)

[wherein ----- represents a double bond or single bond; $R^1$ represents $C_1$-$C_5$ alkyl, $C_4$-$C_7$ cycloalkylalkyl, $C_5$-$C_7$ cycloalkenylalkyl, $C_6$-$C_{12}$ aryl, $C_7$-$C_{13}$ aralkyl, $C_4$-$C_7$ alkenyl, allyl, $C_1$-$C_5$ furan-2-ylalkyl or $C_1$-$C_5$ thiophene-2-ylakyl; $R^2$ represents hydrogen, hydroxy, nitro, $C_1$-$C_5$ alkanoyloxy, $C_1$-$C_5$ alkoxy, $C_1$-$C_5$ alkyl or —$NR^9R^{10}$ wherein $R^9$ represents hydrogen or $C_1$-$C_5$ alkyl and $R^{10}$ represents hydrogen or $C_1$-$C_5$ alkyl or —C(=O)$R^{11}$ wherein $R^{11}$ represents hydrogen, phenyl or $C_1$-$C_5$ alkyl; $R^3$ represents hydrogen, hydroxy, $C_1$-$C_5$ alkanoyloxy or $C_1$-$C_5$ alkoxy; A represents —XC(=Y)—, —XC(=Y)Z-, —X— or —$XSO_2$— (wherein X, Y and Z independently represent $NR^4$, S or O wherein $R^4$ represents hydrogen, $C_1$-$C_5$ linear or branched alkyl or $C_6$-$C_{12}$ aryl, $R^4$s in the formula may be the same or different); B represents valence bond, $C_1$-$C_{14}$ linear or branched alkylene (with the proviso that said alkylene may have at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl and phenoxy, and that 1 to 3 methylene groups in said alkylene may be substituted with carbonyl group(s)), $C_2$-$C_{14}$ linear or branched acyclic unsaturated hydrocarbon containing 1 to 3 double bonds and/or triple bonds (with the proviso that said acyclic unsaturated hydrocarbon may have at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl and phenoxy, and that 1 to 3 methylene groups in said acyclic unsaturated hydrocarbon may be substituted with carbonyl group(s)), or $C_1$-$C_{14}$ linear or branched saturated or unsaturated hydrocarbon containing 1 to 5 thioether bonds, ether bonds and/or amino bonds (with the proviso that a hetero atom does not directly binds to A, and that 1 to 3 methylene groups in said acyclic unsaturated hydrocarbon may be substituted with carbonyl group(s)); $R^5$ represents hydrogen or an organic group having a skeleton selected from those shown below

Q: NH, O, S

T: $CH_2$, NH, S, O
l = 0–5
m, n ≥ 0
m + n ≤ 5

(wherein Q represents NH, O or S; T represents $CH_2$, NH, S or O; l represents an integer of 0 to 5; and m and n independently represent integers of not less than 0, the total of m and n being not more than 5; each of said organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy); $R^6$ represents hydrogen; $R^7$ represents hydrogen, hydroxy, $C_1$-$C_5$ alkoxy or $C_1$-$C_5$ alkanoyloxy; or $R^6$ and $R^7$ cooperatively represent —O—, —$CH_2$— or —S—; and $R^8$ represents hydrogen, $C_1$-$C_5$ alkyl or $C_1$-$C_5$ alkanoyl]
or a pharmaceutically acceptable acid addition salt thereof.

In Formula (I), as $R^1$, $C_1$-$C_5$ alkyl, $C_4$-$C_7$ cycloalkylmethyl, $C_5$-$C_7$ cycloalkenylmethyl, $C_7$-$C_{13}$ phenylalkyl, $C_4$-$C_7$ alkenyl, allyl, $C_1$-$C_5$ furan-2-yl-alkyl and $C_1$-$C_5$ thiophene-2-yl-alkyl are preferred, and methyl, ethyl, propyl, butyl, isobutyl, cyclopropylmethyl, allyl, benzyl, phenethyl, furan-2-yl-methyl and thiophene-2-yl-methyl are especially preferred.

As $R^2$, hydrogen, hydroxy, nitro, acetoxy, methoxy, methyl, ethyl, propyl, amino, dimethylamino, acetylamino and benzoylamino are preferred. Among these, hydrogen, hydroxy, nitro, acetoxy, methoxy and dimethylamino are preferred, and hydrogen, hydroxy, acetoxy and methoxy are particularly preferred.

As $R^3$, hydrogen, hydroxy, acetoxy and methoxy preferred, and hydroxy, acetoxy and methoxy are especially preferred.

Examples of the groups represented by A include —$NR^4C$(=O)—, —$NR_4C$(=S)—, —$NR^4C$(=O)O—, —$NR_4C$(=O)$NR^4$—, —$NR^4C$(=S)$NR^4$-, —$NR_4C$(=O)S—, —OC(=O)—OC(=O)O—, —SC(=O)—, —$NR^4$—, —, —$NR^4SO_2$—, —$OSO_2$— and the like. As A, —XC(=Y)— (wherein X represents $NR^4$, S or O; Y represents O wherein $R^4$ represents hydrogen or $C_1$-$C_5$ alkyl), —XC(=Y)Z-, —X— and —$XSO_2$— (wherein X represents $NR^4$, Y represents O or S, Z represents $NR^4$ or O wherein $R^4$ represents hydrogen or $C_1$-$C_5$ alkyl) are preferred. Among these, —NRC(=O)—, —$NR^4C$(=S)—, —$NR^4C$(=O)O—, —$NR^4C$(=O)$NR^4$—, —$NR^4C$(=S)$NR^4$— and —$NR^4SO_2$— are particularly preferred, —$NR^4C$(=O)—, —$NR^4C$(=O)$NR^4$— and —$NR^4C$(=O)O— are more preferred, and —$NR^4C$(=O)— and —$NR^4C$(=O)$NR^4$— are especially preferred.

As $R^4$, hydrogen and $C_1$-$C_5$ linear or branched alkyl are preferred. Especially, $C_1$-$C_5$ linear or branched alkyl are preferred, and among these, methyl, ethyl, propyl, butyl and isobutyl are preferred.

As B, —$(CH_2)_n$-(n=0-10), —$(CH_2)_n$—C(=O)-(n=1-4), —CH=CH—$(CH_2)_n$-(n=0-4), —C≡C—$(CH_2)_n$-(n=0-4), —$CH_2$—O—, —$CH_2$—S—, —$CH_2$—NH—, —$(CH_2)_2$—O—$CH_2$— and —CH=CH—CH=CH—$(CH_2)_n$-(n=0-4)

are preferred, and —(CH$_2$)$_n$—(n=1-3), —CH=CH—(CH$_2$)$_n$- (n=0-4), —C≡C—(CH$_2$)$_n$—(n=0-4), —CH$_2$—O—, —CH$_2$—S— and —CH$_2$—NH— are especially preferred. Among these, C$_1$-C$_3$ linear alkylene, —CH=CH—, —C≡C—, —CH$_2$O—, —CH$_2$S— and —CH$_2$—NH— are preferred, and —CH=CH— and —C≡C— are especially preferred (needless to say, these preferred examples include those having the above-described substituents).

As R$^5$, hydrogen and organic groups having skeletons shown below

Q: O, S

(wherein Q represents O or S; each of said organic groups may have at least one substituent selected from the group consisting of C$_1$-C$_5$ alkyl, C$_1$-C$_5$ alkoxy, C$_1$-C$_5$ alkanoyloxy, hydroxy, fluorine, chlorine, bromine, iodine, amino, nitro, cyano, isothiocyanato, trifluoromethyl, trifluoromethoxy and methylenedioxy) are preferred. Among these, hydrogen, phenyl, thienyl, and furanyl (each of said organic groups may have at least one substituent selected from the group consisting of C$_1$-C$_5$ alkyl, C$_1$-C$_5$ alkoxy, C$_1$-C$_5$ alkanoyloxy, hydroxy, fluorine, chlorine, bromine, iodine, amino, nitro, cyano, isothiocyanato, trifluoromethyl, trifluoromethoxy and methylenedioxy) are preferred.

More specific preferred examples include hydrogen, phenyl, 2-methylphenyl, 3-methylphenyl, 4-methylphenyl, 3,4-dimethylphenyl, 3,5-dimethylphenyl, 2-methoxyphenyl, 3-methoxyphenyl, 4-methoxyphenyl, 3,4-dimethoxyphenyl, 3,5-dimethoxyphenyl, 3-hydroxyphenyl, 4-hydroxyphenyl, 3,4-dihydroxyphenyl, 2-fluorophenyl, 3-fluorophenyl, 4-fluorophenyl, 3,4-difluorophenyl, perfluorophenyl, 2-chlorophenyl, 3-chlorophenyl, 4-chlorophenyl, 2,4-dichlorophenyl, 3,4-dichlorophenyl, 2,4,5-trichlorophenyl, 2,4,6-trichlorophenyl, 2-bromophenyl, 3-bromophenyl, 4-bromophenyl, 2-nitrophenyl, 3-nitrophenyl, 4-nitrophenyl, 2-aminophenyl, 3-aminophenyl, 4-aminophenyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 3,4-methylenedioxyphenyl, 2-furanyl, 3-furanyl, 2-thienyl, 3-thienyl, cyclopentyl and cyclohexyl, but examples of R$^5$ are not restricted thereto.

R$^6$ and R$^7$ preferably form —O—, —CH$_2$— or —S— cooperatively, and especially preferably form —O— cooperatively.

As R$^8$, hydrogen, C$_1$-C$_5$ alkyl and C$_1$-C$_5$ alkanoyl are preferred. Among these, hydrogen, methyl, ethyl and propyl are preferred, and hydrogen is especially preferred.

Among the compounds represented by Formula (I), preferred are those wherein R$^1$ is methyl, ethyl, propyl, butyl, isobutyl, cyclopropylmethyl, allyl, benzyl or phenethyl; R$^2$ and R$^3$ independently are hydrogen, hydroxy, acetoxy or methoxy; A is —XC(=Y)— (wherein X represents NR$^4$, S or O; Y represents O wherein R$^4$ represents hydrogen or C$_1$-C$_5$ alkyl), —NR$^4$C(=Y)Z- (wherein Y represents O or S; Z represents NR$^4$ or O wherein R$^4$ represents hydrogen or C$_1$-C$_5$ alkyl), —NR$^4$— (wherein R$^4$ represents hydrogen or C$_1$-C$_5$ alkyl) or —NR$^4$XSO$_2$— (wherein R$^4$ represents hydrogen or C$_1$-C$_5$ alkyl); B is C$_1$-C$_3$ linear alkylene, —CH=CH—, —C≡C—, —CH$_2$—O—, —CH$_2$—S— or —CH$_2$—NH—; R$^5$ is hydrogen or an organic group having a skeleton selected from those shown below

Q: O, S (wherein Q represents O or S; each of said organic groups may have at least one substituent selected from the group consisting of C$_1$-C$_5$ alkyl, C$_1$-C$_5$ alkoxy, C$_1$-C$_5$ alkanoyloxy, hydroxy, fluorine, chlorine, bromine, iodine, amino, nitro, cyano, isothiocyanato, trifluoromethyl, trifluoromethoxy and methylenedioxy); R$^6$ and R cooperatively form —O—; and R$^8$ is hydrogen; and more preferred are those wherein R$^1$ is methyl, ethyl, propyl, butyl, isobutyl, cyclopropylmethyl, allyl, benzyl or phenethyl; R$^2$ and R$^3$ independently are hydrogen, hydroxy, acetoxy or methoxy; A is —NR$^4$C(=O)— or —NR$^4$C(=O)O— (wherein R represents C$_1$-C$_5$ alkyl); B is C$_1$-C$_3$ linear alkylene, —CH=CH—, —C≡C—, —CH$_2$—O—, —CH$_2$—S— or —CH$_2$—NH—; R$^5$ is hydrogen or an organic group having a skeleton selected from those shown below

Q: O, S (wherein Q represents O or S; each of said organic groups may have at least one substituent selected from the group consisting of C$_1$-C$_5$ alkyl, C$_1$-C$_5$ alkoxy, C$_1$-C$_5$ alkanoyloxy, hydroxy, fluorine, chlorine, bromine, iodine, amino, nitro, cyano, isothiocyanato, trifluoromethyl, trifluoromethoxy and methylenedioxy); R$^6$ and R$^7$ cooperatively form —O—; and R$^8$ is hydrogen.

The compounds represented by Formula (I) may be produced by the method described in Japanese Patent No. 2525552.

The present invention also provides, particularly, a therapeutic agent for sepsis comprising, as an effective ingredient, an opioid κ receptor agonist compound which is a morphinan quaternary ammonium salt derivative represented by the following Formula (II):

(II)

[wherein ---- represents a double bond or single bond; R$^1$ represents C$_1$-C$_5$ alkyl, C$_4$-C$_7$ cycloalkylalkyl, C$_5$-C$_7$ cycloalkenylalkyl, C$_7$-C$_{13}$ aralkyl, C$_4$-C$_7$ alkenyl or allyl; R$^2$ represents hydrogen, hydroxy, nitro, C$_1$-C$_5$ alkanoyloxy, C$_1$-C$_5$ alkoxy or C$_1$-C$_5$ alkyl; R$^3$ represents hydrogen, hydroxy, C$_1$-C$_5$ alkanoyloxy or C$_1$-C$_5$ alkoxy; R$^4$ represents hydrogen, C$_1$-C$_5$ linear or branched alkyl or C$_6$-C$_{12}$ aryl; A represents $C_1$-$C_6$ alkylene, —CH=CH— or —C≡C—; $R^5$ represents hydrogen or an organic group having a skeleton selected from those shown below (wherein Q represents O or S; T represents $CH_2$, NH, S or O; l represents an integer of 0 to 5; and m and n independently represent integers of not less than 0, the total of m and n being not more than 5; each of said organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, nitro, cyano, isothiocyanato, trifluoromethyl, trifluoromethoxy and methylenedioxy);

$R^6$ represents $C_1$-$C_5$ alkyl or allyl; and $X^-$ represents a pharmaceutically acceptable counter ion].

In Formula (II), as $R^1$, $C_1$-$C_5$ alkyl, $C_4$-$C_7$ cycloalkylalkyl, $C_5$-$C_7$ cycloalkenylalkyl, $C_7$-$C_{13}$ aralkyl, $C_4$-$C_7$ alkenyl and allyl are preferred, and methyl, ethyl, propyl, butyl, isobutyl, cyclopropylmethyl, cyclobutylmethyl, cyclopentylmethyl, cyclopentenylmethyl, cyclohexenylmethyl, benzyl, phenethyl, trans-2-butenyl, 2-methyl-2-butenyl and allyl are especially preferred. More preferred are methyl, ethyl, propyl, butyl, isobutyl, cyclopropylmethyl, benzyl, phenethyl and allyl.

As $R^2$, hydrogen, hydroxy, nitro, acetoxy, methoxy, methyl, ethyl and propyl are preferred, and hydrogen, hydroxy, acetoxy and methoxy are particularly preferred.

As $R^3$, hydrogen, hydroxy, $C_1$-$C_5$ alkanoyloxy and $C_1$-$C_5$ alkoxy are preferred, and hydrogen, hydroxy, acetoxy and methoxy are particularly preferred.

As $R^4$, hydrogen, $C_1$-$C_5$ linear or branched alkyl and $C_6$-$C_{12}$ aryl are preferred, and $C_1$-$C_5$ linear or branched alkyl, particularly, methyl, ethyl, propyl, isopropyl, butyl and isobutyl are especially preferred.

As A, $C_1$-$C_6$ alkylene, —CH=CH— and —C≡C— are preferred, and —CH=CH— and —C≡C— are particularly preferred.

As $R^5$, hydrogen and organic groups having skeletons shown below (wherein Q represents O or S; each of said organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy) are preferred. Especially preferred are phenyl, 2-chlorophenyl, 3-chlorophenyl, 4-chlorophenyl, 3,4-dichlorophenyl, 2-fluorophenyl, 3-fluorophenyl, 4-fluorophenyl, 3,4-difluorophenyl, 2-bromophenyl, 3-bromophenyl, 4-bromophenyl, 2-nitrophenhyl, 3-nitrophenhyl, 4-nitrophenhyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 2-methylphenyl, 3-methylphenyl, 4-methylphenyl, 3,4-dimethylphenyl, 2-methoxyphenyl, 3-methoxyphenyl, 4-methoxyphenyl, 3,4-dimethoxyphenyl, 3,5-dimethoxyphenyl, 2-hydroxyphenyl, 3-hydroxyphenyl, 4-hydroxyphenyl, 3,4-dihydroxyphenyl, 3-furanyl, 2-furanyl, 3-thienyl, 2-thienyl, cyclopentyl and cyclohexyl, but examples of $R^5$ are not restricted thereto.

As $R^6$, $C_1$-$C_5$ alkyl and allyl are preferred, and methyl is especially preferred.

As the pharmaceutically preferred counterion $X^-$, iodide ion, bromide ion, chloride ion, methanesulfonate and the like are preferred, but, needless to say, $X^-$ is not restricted thereto.

Among the compounds represented by Formula (II), those wherein $R^1$ is methyl, ethyl, propyl, butyl, isobutyl, cyclopropylmethyl, allyl, benzyl or phenethyl; $R^2$ and $R^3$ independently are hydrogen, hydroxy, acetoxy or methoxy; $R^4$ is hydrogen or $C_1$-$C_5$ linear or branched alkyl; A is —CH=CH— or —C≡C—; $R^5$ is an organic group having a skeleton selected from those shown below (wherein Q represents O or S; each of said organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, nitro, cyano, isothiocyanato, trifluoromethyl, trifluoromethoxy and methylenedioxy);

$R^6$ is methyl; and $X^-$ is iodide ion, are preferred.

The compounds represented by Formula (II) may be produced by the method described in WO98/23290.

The present invention also provides, particularly, a therapeutic agent for sepsis comprising, as an effective ingredient, an opioid κ receptor agonist compound which is morphinan-N-oxide derivative represented by the following Formula (III):

[wherein ----- represents a double bond or single bond; $R^1$ represents $C_1$-$C_5$ alkyl, $C_4$-$C_7$ cycloalkylalkyl, $C_5$-$C_7$ cycloalkenylalkyl, $C_6$-$C_{12}$ aryl, $C_7$-$C_{13}$ aralkyl, $C_4$-$C_7$ alkenyl or allyl; R2 represents hydrogen, hydroxy, nitro, $C_1$-$C_5$ alkanoyloxy, $C_1$-$C_5$ alkoxy or $C_1$-$C_5$ alkyl; $R^3$ represents hydrogen, hydroxy, $C_1$-$C_5$ alkanoyloxy or $C_1$-$C_5$ alkoxy; $R^4$ represents hydrogen, $C_1$-$C_5$ linear or branched alkyl or $C_6$-$C_{12}$ aryl; A represents $C_1$-$C_6$ alkylene, —CH=CH— or —C≡C—; $R^5$ represents hydrogen or an organic group having a skeleton selected from those shown below (wherein T represents $CH_2$ or O; l represents an integer of 0 to 5; and m and n independently represent integers of not less than 0, the total of m and n being not more than 5; each of said organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, nitro, cyano, isothiocyanato, trifluoromethyl, trifluoromethoxy and methylenedioxy)] or a pharmaceutically acceptable acid addition salt thereof.

In Formula (III), as $R^1$, $C_1$-$C_5$ alkyl, $C_4$-$C_7$ cycloalkylalkyl, $C_5$-$C_7$ cycloalkenylalkyl, $C_7$-$C_{13}$ aralkyl, $C_4$-$C_7$ alkenyl and allyl are preferred, and methyl, ethyl, propyl, butyl, isobutyl, cyclopropylmethyl, cyclobutylmethyl, cyclopentylmethyl, cyclopentenylmethyl, cyclohexenylmethyl, benzyl, phenethyl, trans-2-butenyl, 2-methyl-2-butenyl and allyl are especially preferred. More preferred are methyl, ethyl, propyl, butyl, isobutyl, cyclopropylmethyl, benzyl, phenethyl and allyl.

As $R^2$, hydrogen, hydroxy, nitro, acetoxy, methoxy, methyl, ethyl and propyl are preferred, and hydrogen, hydroxy, acetoxy and methoxy are particularly preferred.

As $R^3$, hydrogen, hydroxy, acetoxy and methoxy are preferred.

As $R^4$, hydrogen, $C_1$-$C_5$ linear or branched alkyl and phenyl are preferred, and $C_1$-$C_5$ linear or branched alkyl are especially preferred. Among these, methyl, ethyl, propyl, isopropyl butyl and isobutyl are particularly preferred.

As A, $C_1$-$C_6$ alkylene, —CH=CH— and —C≡C— are preferred, and —CH=CH— and —C≡C— are particularly preferred.

As $R^5$, hydrogen and organic groups having skeletons shown below

(each of said organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, nitro, cyano, isothiocyanato, trifluoromethyl, trifluoromethoxy and methylenedioxy) are preferred. Especially preferred are phenyl, 2-chlorophenyl, 3-chlorophenyl, 4-chlorophenyl, 3,4-dichlorophenyl, 2-fluorophenyl, 3-fluorophenyl, 4-fluorophenyl, 3,4-difluorophenyl, 2-bromophenyl, 3-bromophenyl, 4-bromophenyl, 2-nitrophenhyl, 3-nitrophenhyl, 4-nitrophenhyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 2-methylphenyl, 3-methylphenyl, 4-methylphenyl, 2-methoxyphenyl, 3-methoxyphenyl, 4-methoxyphenyl, 3,4-dimethoxyphenyl, 3,5-dimethoxyphenyl, 3-furanyl, 2-furanyl, cyclopentyl and cyclohexyl, but, needless to say, $R^5$ is not restricted to these examples.

Among the compounds represented by Formula (III), preferred are those wherein $R^1$ is methyl, ethyl, propyl, butyl, isobutyl, cyclopropylmethyl, allyl, benzyl or phenethyl; $R^2$ and $R^3$ independently are hydrogen, hydroxy, acetoxy or methoxy; $R^4$ is hydrogen or $C_1$-$C_5$ linear or branched alkyl; A is —CH=CH— or —C≡C—; $R^5$ is an organic group having a skeleton selected from those shown below (each of said organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, nitro, cyano, isothiocyanato, trifluoromethyl, trifluoromethoxy and methylenedioxy).

The present invention also provides, particularly, a therapeutic agent for sepsis comprising, as an effective ingredient, an opioid κ receptor agonist compound which is represented by the following Formula (IV):

[wherein the wavy lines (~) between the cyclohexane ring and the two nitrogen atoms represent bonds which are cis or trans with respect to the cyclohexane ring; A represents valence bond, —$(CH_2)_q$—, —$CH(CH_3)$— or —X$(CH_2)_n$— (wherein q represents an integer of 1 to 4; n represents an integer of 1 to 4; and X represents O or S); Ar represents a carbocyclic aromatic ring, heterocyclic aromatic ring, bicarbocyclic aromatic ring, tricarbocyclic aromatic ring or diphenylmethyl, each of said carbocyclic aromatic ring, heterocyclic aromatic ring, bicarbocyclic aromatic ring, tricarbocyclic aromatic ring and diphenylmethyl may have one or more substituents selected from the group consisting of hydrogen, halogen, trifluoromethyl, nitro, $C_1$-$C_3$ alkoxy, hydroxy, azide, $C_1$-$C_3$ alkyl, methanesulfonyl, cyano, amino, $C_1$-$C_3$ alkoxycarbonyl, $C_1$-$C_3$ alkanoyloxy and $C_1$-$C_3$ acylamino represented by —NHC(=O)$R^7$ (wherein $R^7$ represents hydrogen or $C_1$-$C_2$ alkyl); R represents hydrogen, $C_1$-$C_3$ alkyl or allyl; $R^1$ and $R^2$ independently represent hydrogen, $C_1$-$C_3$ alkyl or allyl, or $R^1$, $R^2$ and the nitrogen atom to which they bind cooperatively represent azetidinyl, pyrrolidinyl, 3-hydroxypyrrolidinyl, 3-fluoropyrrolidinyl, morpholinyl, piperidinyl or 3,4-dehydropiperidinyl; $R^3$, $R^4$, $R^5$ and $R^6$ independently represent hydrogen, hydroxy, $OR^8$ or $OC(=O)R^9$, or $R^5$ and $R^6$ cooperatively represent -E-CH$_2$—CH$_2$-E-, =E, —CH$_2$—CH$_2$—CH$_2$-Z- or —CH$_2$—CH$_2$-Z-CH$_2$— (wherein Z represents oxygen (—O—), —NR$^{10}$—, sulfur (—S—), —S(=O)— or —S(=O)$_2$—; E represents N—OH, N—OC(=O)CH$_3$, oxygen or sulfur; $R^8$ represents $C_1$-$C_3$ alkyl; and $R^9$ represents hydrogen or $C_1$-$C_3$ alkyl]
or a pharmaceutically acceptable acid addition salt thereof.
Among the compounds represented by Formula (IV), the following compounds are preferred:
- (±)—N-[2-(N,N-dimethylamino)cyclohexyl]-N-methyl-2-(4-trifluoromethylphenyl)acetamide,
- (±)—N-[2-(N,N-dimethylamino)cyclohexyl]-N-propyl-2-(3-methoxyphenyl)acetamide,
- (±)—N-[2-(N,N-dimethylamino)cyclohexyl]-N-methyl-2-(4-azidophenyl)acetamide,
- (±)—N-[2-(N,N-dimethylamino)cyclohexyl]-N-methyl-2-(3,4-dichlorophenyl)acetamide,
- (±)—N-[2-(N,N-dimethylamino)cyclohexyl]-N-methyl-2-(4-methoxyphenyl)acetamide,
- (±)—N-[2-(N,N-dimethylamino)cyclohexyl]-N-methyl-2-(2-naphthyl)acetamide,
- (±)—N-[2-(N-cyclopropyl-N-methylamino)cyclohexyl]-N-methyl-2-(4-azidophenyl)acetamide,
- (±)—N-[2-(3-acetoxy-1-pyrrolidinyl)cyclohexyl]-N-methyl-2-(3,4-dichlorophenyl)acetamide,
- (±)—N-[2-(N-pyrrolidinyl)cyclohexyl]-N-methyl-2-(3,4-dichlorophenyl)acetamide,
- (±)—N-[2-(3-hydroxypyrrolidinyl)cyclohexyl]-N-methyl-2-(3,4-dichlorophenyl)acetamide,
- (±)—N-[2-(N-(3-hydroxy-1-azetidinyl))cyclohexyl]-N-methyl-2-(3,4-dichlorophenyl)acetamide,
- (±)—N-[2-(N,N-diethylamino)cyclohexyl]-N-methyl-2-(3,4-dichlorophenyl)acetamide,
- (±)—N-[2-(N-pyrrolidinyl)cyclohexyl]-N-methyl-2-(3,4-dichlorophenyl)propionamide,
- (±)—N-[2-(4-methyl-1-piperazinyl)cyclohexyl]-2-(3,4-dichlorophenyl)acetamide,
- (±)—N-[2-(N,N-dimethylamino)cyclohexyl]-2-(3,4-dichlorophenyl)acetamide,
- (±)-3,4-dichloro-N-methyl-N-[8-(1-pyrrolidinyl)-1,4-dioxaspiro[4.5]dec-7-yl]benzacetamide,
- (±)-3,4-dichloro-N-methyl-N-[7-(1-pyrrolidinyl)-1,4-dioxaspiro[4.5]dec-8-yl]benzacetamide,
- (±)-3,4-dichloro-N-methyl-N-[7-(1-pyrrolidinyl)-1,4-dioxaspiro[4.5]dec-6-yl]benzacetamide,
- (±)-4-bromo-N-methyl-N-[7-(1-pyrrolidinyl)-1,4-dioxaspiro[4.5]dec-8-yl]benzacetamide,
- (±)-3-fluoro-N-ethyl-N-[7-(1-azetidinyl)-1,4-dioxaspiro[4.5]dec-8-yl]benzacetamide,
- (±)-3,4-dichloro-N-methyl-N-[7-(1-pyrrolidinyl)-1,4-dioxaspiro[4.4]non-8-yl]benzacetamide,
- (±)-3,4-dichloro-N-methyl-N-[7-(1-pyrrolidinyl)-1,4-dioxaspiro[4.6]undec-8-yl]benzacetamide,
- (±)-3,4-dichloro-N-methyl-N-[8-(1-pyrrolidinyl)-1,4-dioxaspiro[4.6]undec-7-yl]benzacetamide,
- (±)-3,4-dichloro-N-methyl-N-[9-(1-pyrrolidinyl)-1,4-dioxaspiro[4.6]undec-8-yl]benzacetamide,
- (±)-3,4-dichloro-N-[4-methoxy-2-(1-pyrrolidinyl)cyclohexyl]-N-methylbenzacetamide,
- (±)-3,4-dichloro-N-[5-methoxy-2-(1-pyrrolidinyl)cyclohexyl]-N-methylbenzacetamide,
- (±)-3,4-dichloro-N-methyl-N-[4-oxo-2-(1-pyrrolidinyl)cyclohexyl]benzacetamide,
- (±)-4-bromo-N-methyl-N-[2-(N,N-dimethylamino)-4-oxocyclohexyl]benzacetamide,
- (±)—N-[4-acetyloxy-2-(1-pyrrolidinyl)cyclohexyl]-3,4-dichloro-N-methylbenzacetamide,
- (±)—N-[4-acethyloxy-2-aminocyclohexyl]-3,4-difluoro-N-methylbenzacetamide,
- (±)-3,4-dichloro-N-[5-(hydroxyimino)-2-(1-pyrrolidinyl)cyclohexyl]-N-methylbenzacetamide,
- (±)-3,4-dichloro-N-[4,4-dimethoxy-2-(1-pyrrolidinyl)cyclohexyl]-N-methylbenzacetamide
- (±)-3,4-dichloro-N-[4,4-dimethoxy-2-(1-pyrrolidinyl)cyclohexyl]-N-methylbenzacetamide (or (±-3,4-dichloro-N-methyl-N-[4-oxo-2-(1-pyrrolidinyl)cyclohexyl]benzacetamide dimethylketal),
- (±)-3,4-dichloro-N-[5,5-diethoxy-2-(1-pyrrolidinyl)cyclohexyl]-N-methylbenzacetamide,
- (±)-(1α,2β)-3,4-dichloro-N-[4,4-dimethoxy-2-(pyrrolidinyl)cyclohexyl]-N-methylbenzacetamide,
- (±)-4-trifluoromethyl-N-[4,4-dimethoxy-2-(1-pyrrolidinyl)cyclohexyl]-N-methylbenzacetamide,
- (±)-3-trifluoromethyl-N-[4,4-dimethoxy-2-(1-pyrrolidinyl)cyclohexyl]-N-methylbenzacetamide,
- (±)-3-hydroxy-4-methyl-N-[4,4-dimethoxy-2-(1-pyrrolidinyl)cyclohexyl]-N-methylbenzacetamide,
- (±)-4-methanesulfonyl-N-[4,4-dimethoxy-2-(1-piperidinyl)cyclohexyl]-N-methylbenzamide,
- (±)-4-acetyloxy-N-[4,4-dimethoxy-2-(1-pyrrolidinyl)cyclohexyl]-N-methylbenzacetamide,
- (±)—N-[4,4-bis(methylthio)-2-(1-pyrrolidinyl)cyclohexyl]-3,4-dichloro-N-methylbenzacetamide,
- (±)—N-[5,5-bis(ethylthio)-2-(1-pyrrolidinyl)cyclohexyl]-3,4-dichloro-N-methylbenzacetamide,
- (±)-3,4-dichloro-N-[4-methylthio-2-(1-pyrrolidinyl)cyclohexyl]-N-methylbenzacetamide,
- (±)-3,4-dichloro-N-[5-ethylthio-2-(1-pyrrolidinyl)cyclohexyl]-N-methylbenzacetamide,
- (±)-3,4-dichloro-N-[6-methylthio-2-(1-pyrrolidinyl)cyclohexyl]-N-methylbenzacetamide,
- (±)-3,4-dichloro-N-[4-mercapto-2-(1-pyrrolidinyl)cyclohexyl]-N-methylbenzacetamide,
- [1R-(1α,2β,4β,5β)]-N-[4,5-dimethoxy-2-(1-pyrrolidinyl)cyclohexyl]-N-methyl-4-benzofuranacetamide,
- [1S-(1α,2β,4β,5β)]-N-[4,5-dimethoxy-2-(1-pyrrolidinyl)cyclohexyl]-N-methyl-4-benzofuranacetamide,
- [1R-(1α,2β,4α,5α)]-N-[4,5-dimethoxy-2-(1-pyrrolidinyl)cyclohexyl]-N-methyl-4-benzofuranacetamide,
- [1S-(1α,2β,4α,5α)]-N-[4,5-dimethoxy-2-(1-pyrrolidinyl)cyclohexyl]-N-methyl-4-benzofuranacetamide,
- [1R-(1α,2β,4β,5β)]-N-[4,5-dimethoxy-2-(1-pyrrolidinyl)cyclohexyl]-N-methylbenzo[b]thiophen-4-acetamide,
- [1S-(1α,2β,4β,5β)]-N-[4,5-dimethoxy-2-(1-pyrrolidinyl)cyclohexyl]-N-methylbenzo[b]thiophen-4-acetamide,
- [1R-(1α,2β,4α,5α)]-N-[4,5-dimethoxy-2-(1-pyrrolidinyl)cyclohexyl]-N-methylbenzo[b]thiophen-4-acetamide,
- [1S-(1α,2β,4α,5α)]-N-[4,5-dimethoxy-2-(1-pyrrolidinyl)cyclohexyl]-N-methylbenzo[b]thiophen-4-acetamide,
- [1R-(1α,2β,4β,5β)]-N-[4,5-dimethoxy-2-(1-pyrrolidinyl)cyclohexyl]-N-methyl-1-naphthaleneacetamide,
- [1S-(1α,2β,4α,5α)]-N-[4,5-dimethoxy-2-(1-pyrrolidinyl)cyclohexyl]-N-methyl-1-naphthaleneacetamide,
- [1R-(1α,2β,4α,5α)]-N-[4,5-dimethoxy-2-(1-pyrrolidinyl)cyclohexyl]-N-methyl-1-naphthaleneacetamide,
- [1S-(1α,2β,4β,5β)]-N-[4,5-dimethoxy-2-(1-pyrrolidinyl)cyclohexyl]-N-methyl-1-naphthaleneacetamide,
- [1R-(1α,2β,4β,5β)]-3,4-dichloro-N-[4,5-dimethoxy-2-(1-pyrrolidinyl)cyclohexyl]-N-methylbenzacetamide,

[1S-(1α,2β,4β,5β)]-3,4-dichloro-N-[4,5-dimethoxy-2-(1-pyrrolidinyl)cyclohexyl]-N-methylbenzacetamide,
[1R-(1α,2β,4α,5α)]-3,4-dichloro-N-[4,5-dimethoxy-2-(1-pyrrolidinyl)cyclohexyl]-N-methyl benzacetamide,
[1S-(1α,2β,4α,5α)]-3,4-dichloro-N-[4,5-dimethoxy-2-(1-pyrrolidinyl)cyclohexyl]-N-methylbenzacetamide,
[1R-(1α,2β,4β,5β)]-N-[4,5-dimethoxy-2-(1-pyrrolidinyl)cyclohexyl]-N-methyl-9H-fluorene-9-carboxamide,
[1S-(1α,2β,4β,5β)]-N-[4,5-dimethoxy-2-(pyrrolidinyl)cyclohexyl]-N-methyl-9H-fluorene-9-carboxamide,
[1R-(1α,2β,4α,5α)]-N-[4,5-dimethoxy-2-(1-pyrrolidinyl)cyclohexyl]-N-methyl-9H-fluorene-9-carboxamide,
[1S-(1α,2β,4α,5α)]-N-[4,5-dimethoxy-2-(1-pyrrolidinyl)cyclohexyl]-N-methyl-9H-fluorene-9-carboxamide,
(±)-(1α,2β,4β)-N-methyl-N-[4-methoxy-2-(1-pyrrolidinyl)cyclohexyl]-4-benzofuranacetamide,
(±)-(1α,2β,4α)-N-methyl-N-[4-methoxy-2-(1-pyrrolidinyl)cyclohexyl]-4-benzofuranacetamide,
(±)-(1α,2β,5β)—N-methyl-N-[5-methoxy-2-(1-pyrrolidinyl)cyclohexyl]-4-benzofuranacetamide,
(±)-(1α,2β,5α)-N-methyl-N-[5-methoxy-2-(1-pyrrolidinyl)cyclohexyl]-4-benzofuranacetamide,
(±)-(1α,2β,4α)-N-[4-methoxy-2-(1-pyrrolidinyl)cyclohexyl]-N-methyl-9H-fluorene-9-carboxamide,
(±)-(1α,2β,5β)-N-[5-methoxy-2-(1-pyrrolidinyl)cyclohexyl]-N-methyl-9H-fluorene-9-carboxamide,
(±)—N-methyl-2-(1-naphthalenyloxy)-N-[2-(1-pyrrolidinyl)cyclohexyl]acetamide,
(±)—N-methyl-2-(2-naphthalenyloxy)-N-[2-(1-pyrrolidinyl)cyclohexyl]acetamide,
(±)-1,2-dihydro-N-methyl-N-[2-(1-pyrrolidinyl)cyclohexyl]-1-acenaphthylenecarboxamide (isomer I. mixture of (1α,2β) and (1β,2α)),
(±)-1,2-dihydro-N-methyl-N-[2-(1-pyrrolidinyl)cyclohexyl]-1-acenaphthylenecarboxamide (isomer II. mixture of (1α,2β) and (1β,2α)),
(±)—N-[4,5-dimethoxy-2-(1-pyrrolidinyl)cyclohexyl]-1,2-dihydro-N-methyl-1-acenaphthylenecarboxamide (isomer I. mixture of(1α,2β,4β,5β) and (1β,2α,4α,5α)),
(±)-1,2-dihydro-N-[4-methoxy-2-(pyrrolidinyl)cyclohexyl]-N-methyl-1-acenaphthylenecarboxamide (isomer I. mixture of (1α,2β,4β) and (1β,2α,4α)),
(±)-1,2-dihydro-N-[4-methoxy-2-(1-pyrrolidinyl)cyclohexyl]-N-methyl-1-acenaphthylenecarboxamide (isomer II. mixture of (1α,2β,4β) and (1β,2α,4α)),
(±)-1,2-dihydro-N-[4-methoxy-2-(1-pyrrolidinyl)cyclohexyl]-N-methyl-1-acenaphthylenecarboxamide (isomers I and II. mixture of (1α,2β,4β) and (1α,2β,4α)),
(±)-1,2-dihydro-N-[4-methoxy-2-(1-pyrrolidinyl)cyclohexyl]-N-methyl-1-acenaphthylenecarboxamide (isomers I and II. mixture of (1β,2α,4α) and (1α,2β,4β)),
(±)-trans-N-methyl-N-[2-(1-pyrrolidinyl)cyclohexyl]-9H-fluorene-9-carboxamide,
(±)-trans-1,3-dihydro-1-oxo-N-methyl-N-[2-(1-pyrrolidinyl)cyclohexyl]-4-isobenzofuranacetamide,
(±)-(1α,2β,4β,5β)-N-[4,5-dimethoxy-2-(1-pyrrolidinyl)cyclohexyl]-1,3-dihydro-N-methyl-1-oxo-4-isobenzofuranacetamide,
(±)-(5α,7α,8β)-3,4-dichloro-N-methyl-N-[7-(1-pyrrolidinyl)-1-oxaspiro [4.5] dec-8-yl]benzacetamide,
(±)-(5α,7β,8β)-bromo-N-methyl-N-[7-(1-pyrrolidinyl)-1-oxaspiro[4.5]dec-8-yl]benzacetamide,
(±)-(5α,7α,8β)-4-methoxy-N-methyl-N-[7-(1-pyrrolidinyl)-1-oxaspiro[4.5]dec-8-yl]benzacetamide,
(±)-(5α,7α,8β)—N-methyl-2-nitro-N-[7-(1-pyrrolidinyl)-1-oxaspiro[4.5]dec-8-yl]benzacetamide,
(±)-(5α,7α,8β)—N-methyl-3-nitro-N-[7-(1-pyrrolidinyl)-1-oxaspiro[4.5]dec-8-yl]benzacetamide,
(±)-(5α,7α,8β)-N-methyl-4-nitro-N-[7-(1-pyrrolidinyl)-1-oxaspiro[4.5]dec-8-yl]benzacetamide,
(±)-(5α,7α,8β)-N-methyl-N-[7-(1-pyrrolidinyl)-1-oxaspiro[4.5]dec-8-yl]-3-(trifluoromethyl)benzacetamide,
(±)-(5α,6α,7β)-3,4-dichloro-N-methyl-N-[7-(1-pyrrolidinyl)-1-oxaspiro[4.5]dec-6-yl]benzacetamide,
(±)-(5α,7α,8β)-3,4-dichloro-N-methyl-N-[7-(1-pyrrolidinyl)-1-thiaspiro[4.5]dec-8-yl]benzacetamide,
(±)-(5α,7β,8α)-3,4-dichloro-N-methyl-N-[8-(1-pyrrolidinyl)-1-oxaspiro[4.5]dec-7-yl]benzacetamide,
(±)-(5α,7α,8β)-3,4-dichloro-N,N-dimethyl-N-[7-(1-pyrrolidinyl)-1-azaspiro[4.5]dec-8-yl]benzacetamide,
(±)-(5α,7α,8β)-4-bromo-N-methyl-N-[7-(1-pyrrolidinyl)-1-azaspiro[4.5]dec-8-yl]benzamide,
(±)-(5α,7α,8β)-3,4-dichloro-N-methyl-N-[7-(1-pyrrolidinyl)-1-thiaspiro[4.5]dec-8-yl]benzamide,
(±)-(5α,7α,8β)-3,4-dichloro-N-methyl-N-[7-(1-pyrrolidinyl)-1-thiaspiro[4.5]dec-8-yl]benzacetamide,
(±)-(5α,7α,8β)-3,4-dichloro-N-methyl-N-[7-(1-pyrrolidinyl)-1-thiaspiro[4.5]dec-8-yl]benzacetamide 1-oxide,
(±)-(5α,7α,8β)-3,4-dichloro-N-methyl-N-[7-(1-pyrrolidinyl)-1-thiaspiro[4.5]dec-8-yl]benzacetamide 1,1-oxide,
(±)-(5α,7α,8β)-N-methyl-N-[7-(1-pyrrolidinyl)-1-azaspiro[4.5]dec-8-yl]-4-trifluoromethylbenzacetamide,
(±)-(5α,7α,8β)—N-methyl-N-[8-(1-pyrrolidinyl)-1-azaspiro[4.5]dec-7-yl]-3-trifluoromethylbenzacetamide,
[(5R)-(5α,7α,8β)]-N-methyl-[7-(1-pyrrolidinyl)-1-oxaspiro[4.5]dec-8-yl]-1H-indene-3-acetamide,
[(5S)-(5α,7α,8β)]-N-methyl-[7-(1-pyrrolidinyl)-1-oxaspiro[4.5]dec-8-yl]-1H-indene-3-acetamide,
[(5R)-(5α,7β,8α)]-N-methyl-[7-(1-pyrrolidinyl)-1-oxaspiro[4.5]dec-8-yl]-1H-indene-3-acetamide,
[(5S)-(5α,7β,8α)]-N-methyl-[7-(1-pyrrolidinyl)-1-oxaspiro[4.5]dec-8-yl]-1H-indene-3-acetamide,
[(5R)-(5α,7α,8β)]-N-methyl-N-[7-(1-pyrrolidinyl)-1-oxaspiro[4.5]dec-8-yl]-1H-indole-3-acetamide,
[(5S)-(5α,7α,8β)]-N-methyl-N-[7-(1-pyrrolidinyl)-1-oxaspiro[4.5]dec-8-yl]-1H-indole-3-acetamide,
[(5R)-(5α,7β,8α)]-N-methyl-N-[7-(1-pyrrolidinyl)-1-oxaspiro[4.5]dec-8-yl]-1H-indole-3-acetamide,
[(5S)-(5α,7α,8α)]-N-methyl-N-[7-(1-pyrrolidinyl)-1-oxaspiro[4.5]dec-8-yl]-1H-indole-3-acetamide,
[(5R)-(5α,7α,8β)]-N-methyl-N-[7-(1-pyrrolidinyl)-1-oxaspiro[4.5]dec-8-yl]-2-benzofuranacetamide,
[(5S)-(5α,7α,8β)]-N-methyl-N-[7-(1-pyrrolidinyl)-1-oxaspiro[4.5]dec-8-yl]-2-benzofuranacetamide,
[(5R)-(5α,7β,8α)]-N-methyl-N-[7-(1-pyrrolidinyl)-1-oxaspiro[4.5]dec-8-yl]-2-benzo[b] furanacetamide,
[(5S)-(5α,7β,8α)]-N-methyl-N-[7-(1-pyrrolidinyl)-1-oxaspiro[4.5]dec-8-yl]-2-benzo[b]futranacetamide,
[(5R)-(5α,7β,8β)]-N-methyl-N-[7-(1-pyrrolidinyl)-1-oxaspiro[4.5]dec-8-yl]-3-benzo[b]furanacetamide,
[(5S)-(5α,7α,8β)]-N-methyl-N-[7-(1-pyrrolidinyl)-1-oxaspiro[4.5]dec-8-yl]-3-benzo[b]furanacetamide,
[(5R)-(5α,7β,8α)]-N-methyl-N-[7-(1-pyrrolidinyl)-1-oxaspiro[4.5]dec-8-yl]-3-benzo[b]furanacetamide,
[(5S)-(5α,7β,8α)]-N-methyl-N-[7-(1-pyrrolidinyl)-1-oxaspiro[4.5]dec-8-yl]-3-benzo[b]furanacetamide,
[(5R)-(5α,7α,8β)]-N-methyl-N-[7-(1-pyrrolidinyl)-1-oxaspiro[4.5]dec-8-yl]-4-benzofuranacetamide,
[(5S)-(5α,7α,8β)]-N-methyl-N-[7-(1-pyrrolidinyl)-1-oxaspiro[4.5]dec-8-yl]-4-benzo[b] furanacetamide,
[(5R)-(5α,7β,8α)]-N-methyl-N-[7-(1-pyrrolidinyl)-1-oxaspiro[4.5]dec-8-yl]-4-benzo[b] furanacetamide,

[(5S)-(5α,7β,8α)]-N-methyl-N-[7-(1-pyrrolidinyl)-1-oxaspiro[4.5]dec-8-yl]-4-benzo[b] furanacetamide,
[(5R)-(5α,7α,8β)]-N-methyl-N-[7-(1-pyrrolidinyl)-1-oxaspiro[4.5]dec-8-yl]-4-benzo[b]thiophene-4-acetamide,
[(5S)-(5α,7α,8β)]-N-methyl-N-[7-(1-pyrrolidinyl)-1-oxaspiro[4.5]dec-8-yl]-4-benzo[b]thiophene-4-acetamide,
[(5R)-(5α,7β,8α)]-N-methyl-N-[7-(1-pyrrolidinyl)-1-oxaspiro[4.5]dec-8-yl]-4-benzo[b]thiophene-4-acetamide,
[(5S)-(5α,7β,8α)]-N-methyl-N-[7-(1-pyrrolidinyl)-1-oxaspiro[4.5]dec-8-yl]-4-benzo[b]thiophene-4-acetamide,
(−)-(5α,7α,8β)—N-methyl-N-[7-(1-pyrrolidinyl)-1-oxaspiro[4.5]dec-8-yl]-4-benzo[b]furanacetamide,
(±)-(5α,7α,8β)-N-[7-(1-pyrrolidinyl)-1-oxaspiro[4.5]dec-8-yl]-4-benzo[b]thiophene-4-acetamide,
(±)-(5α,6α,7β)-3,4-dichloro-N-methyl-N-[7-(1-pyrrolidinyl)-2-oxaspiro[4.5]dec-6-yl]benzacetamide,
(±)-(5α,6α,7β)-3,4-dichloro-N-methyl-N-[6-(1-pyrrolidinyl)-2-oxaspiro[4.5]dec-7-yl]benzacetamide, and
(±)-(5α,7α,8β)-3,4-dichloro-N-methyl-N-[8-(1-pyrrolidinyl)-2-oxaspiro[4.5]dec-7-*yl]benzacetamide, The compounds represented by Formula (IV) may be produced by the methods described in U.S. Pat. No. 4,145,435 (1979), U.S. Pat. No. 4,360,531 (1982), U.S. Pat. No. 4,359,476 (1982), EP Patent No. 108602 (1983), U.S. Pat. No. 4,855,316 (1989), European Patent No. 372466 (1989), European Patent No. 393696 (1990), U.S. Pat. No. 4,906,655 (1990), U.S. Pat. No. 4,438,130 (1984), U.S. Pat. No. 4,663,343 (1987) and U.S. Pat. No. 5,760,023 (1998).

The present invention also provides, particularly, a therapeutic agent for sepsis comprising, as an effective ingredient, an opioid κ receptor agonist compound which is represented by the following Formula (V):

(D)Phe-R1-R2-R3-Q          (V)

[wherein R1 represents (D)NapAla or (D)Phe; R2 represents (D)Nle, Trp or (D)Ile; R3 represents (D)Arg or (D)ChAla; Q is a C-terminal structure of the peptide and represents —(C=O)OH or —(C=O)NXY (wherein X represents hydrogen or $C_1$-$C_6$ alkyl; and Y represents hydrogen or $C_1$-$C_6$ alkyl)]
or a pharmaceutically acceptable acid addition salt thereof.

Among the peptide compounds described above, preferred are (D)Phe-(D)NapAla-(D)Nle-(D)Arg-$NH_2$, (D)Phe-(D)NapAla-(D)Nle-(D)ChAla-$NH_2$, (D)Phe-(D)NapAla-Trp-(D)Arg-$NH_2$, (D)Phe-(D)NapAla-Trp-(D)ChAla-$NH_2$, (D)Phe-(D)NapAla-(D)Ile-(D)Arg-$NH_2$, (D)Phe-(D)NapAla-(D)Ile-(D)ChAla-$NH_2$, (D)Phe-(D)Phe-(D)Nle-(D)Arg-$NH_2$, (D)Phe-(D)Phe-(D)Nle-(D)CIiAla-$NH_2$, (D)Phe-(D)Phe-Trp-(D)Arg-$NH_2$, (D)Phe-(D)Phe-Trp-(D)ChAla-$NH_2$, (D)Phe-(D)Phe-(D)Ile-(D)Arg-$NH_2$ and (D)Phe-(D)Phe-(D)Ile-(D)ChAla-$NH_2$. Peptide compounds described in Japanese Laid-open PCT application No. 11-512075 (1999), in which the C-terminals are not amidized, and the peptide compounds which are amides of which C-terminals are substituted with one or two substituents, as well as pharmaceutically acceptable salts thereof, may also be employed.

Standard procedures for synthesizing peptides are well-known in the art, and the above-described peptide compounds may be prepared by the methods described in Japanese Laid-open PCT application No. 11-512075 (1999) and WO99/32510.

Preferred examples of the pharmaceutically acceptable acid addition salts of the compounds represented by Formulae (I), (III) and (IV) include inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Among these, hydrochloric acid salt, hydrobromic acid salt, phosphoric acid salt, tartaric acid salt and methanesulfonic acid salt are preferred, but the pharmaceutically acceptable acid addition salts are not restricted thereto.

The compounds represented by Formula (I) to (V) or the pharmaceutically acceptable acid addition salts thereof may be administered orally or parenterally as they are or in the form of pharmaceutical compositions after being admixed with known pharmaceutically acceptable acids, carriers or vehicles, after being purified to the level suitable for medical use and after passing the requisite safety tests. Examples of administration forms include injection solutions; oral formulations such as tablets, capsules, granules, powders and syrups; and enteral formulations such as suppositories. The therapeutic agent according to the present invention may preferably contain the above-described effective ingredient at a concentration of 1 to 90% by weight, more preferably 30 to 70% by weight. The administration dose may be appropriately selected depending on the age, bodyweight, administration method and so on. For an adult, the administration dose may be 0.0001 mg to 1 g per day in case of injection solutions, and 0.005 mg to 10 g per day in case of oral formulations, and the drug may be administered once a day or dividedly several times per day.

The compounds represented by Formula (I) to (V) or the pharmaceutically acceptable acid addition salts thereof may be used as an effective ingredient individually or in combination.

The compounds represented by Formula (I) to (V) or the pharmaceutically acceptable acid addition salts thereof may be used together with drugs used for therapy or prevention of sepsis, such as antibiotics, antibacterial agents, anti-endotoxin antibodies, anti-cytokine drugs (including anti-cytokine antibodies, soluble cytokine receptors, inhibitors of cytokine production and cytokine antisense RNAs), or with drugs used for diseases accompanying sepsis, such as steroids; protease inhibitors such as aprotinin, urinastatin, gabexate mesilate and nafamostat mesilate; pentoxifylline and PGG-glucan. They may also be used together with cardiovascular agonists aiming at restoration of circulating blood volume (dopamine, dobutamine, isoproterenol, norepinephrine); diuretics such as furosemide and mannitol; heparins, antithrombin and activated protein C aiming at anti-coagulation; and G-CSF, γ-globulin and the like aiming at promotion of defense. They may also be combined with preventions and therapies used for sepsis or diseases accompanying sepsis, such as endotoxin-adsorption therapy, blood-purification therapy based on dialysis and filtration, nutritional treatment, infusion therapy and the like. The drugs and therapies which may be co-employed are not restricted to those mentioned above.

The diseases to which the therapeutic agent for sepsis according to the present invention is applied include sepsis caused by infections, injury, invasions such as burn and various surgical invasions such as thotacolaparotomy and organ transplantations. Sepsis caused by diseases such as acute pancreatitis, peritonitis, cirrhosis, renal failure, diabetes and dystocia, and by therapies against injury or diseases, such as indwelling catheter, transfusion device and dialysis are also included. Diseases accompanying sepsis, such as organ dysfunction, severe sepsis complicated with hypoperfusion or hypotension, lactic acidosis, hypouresis and septic shock complicated with consciousness disorder are also included. Further, disseminated intravascular coagulation syndrome (DIC), adult respiratory distress syndrome (ARDS), multiple organ dysfunction (MODS) and the like are also included. Further, under special pathological conditions, sepsis accompanying not only intractable blood diseases such as infectious endocarditis, acute leukemia and anaplastic anemia, but also granulocytopenia in therapies accompanying suppression of bone marrow, such as cancer chemotherapies and bone marrow transplantation, and acquired immune deficiency syndrome, are included.

The present invention will now be described more concretely by way of examples.

Example 1

Evaluation of Therapeutic Action against Sepsis

Figure 1:
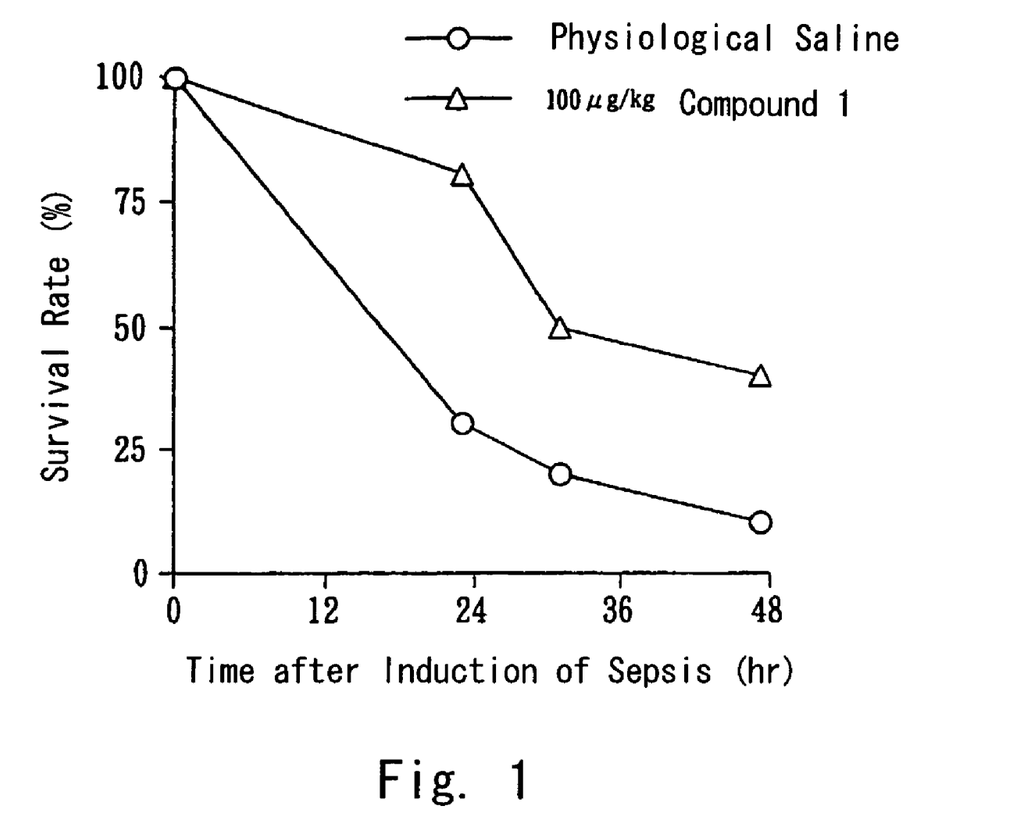
FIG. 1 is a drawing which shows that Compound 1 increases the survival rate of sepsis model animals.

ICR mice (bodyweight of 25g to 35 g when starting the experiments) were raised in a plastic cage under SPF and thermo-hydrostat (22+1° C., 55±5%) conditions under 12-hour light-dark cycle. Foods and water were supplied ad libitum. Lipopolysaccharide (LPS)-induced lethal sepsis which is generally employed as an experimental sepsis model was induced by intrapectoneally administering LPS at a dose of 15 mg/kg. Two hours after administration of LPS when symptoms of sepsis such as diarrhea, worsening of coat of fur and bradykinesia well appeared, (−)-17-(cyclopropylmethyl)-3,14β-dihydroxy-4,5α-epoxy-6 [N-methyl-trans-3-(3-furyl)acrylamide]morphinan hydrochloric acid salt 1 dissolved in physiological saline was subcutaneously administered to the back of each mouse at a dose of 0.1 mg/kg, and the survival of the animals thereafter was tested. To the control group, physiological saline was administered in place of Compound 1. The results are shown in FIG. 1. The survival rate at 24 hours after administration of LPS (induction of sepsis) was 30% in the control group and 80% in the group to which Compound I was administered. The survival rates after 48 hours of the control group and the Compound 1-administered group were 10% and 40%, respectively. Thus, it was shown that Compound 1 has a therapeutic effect against sepsis. Compound 1 may be produced in accordance with the method described in Japanese Patent No. 2525552.

Example 2

Evaluation of Therapeutic Action against Sepsis

ICR mice (bodyweight of 25 g to 35 g when starting the experiments) were raised in a plastic cage under SPF and thermo-hydrostat (22±1° C., 55±5%) conditions under 12-hour light-dark cycle. Foods and water were supplied ad libitum. Lipopolysaccharide (LPS)-induced lethal sepsis which is generally employed as an experimental sepsis model was induced by intrapectoneally administering LPS at a dose of 20 mg/kg. Two hours after administration of LPS when symptoms of sepsis such as diarrhea, worsening of coat of fur and bradykinesia well appeared, (±)—N-[2-(N-pyrrolidinyl)cyclohexyl]-N-methyl-2-(3,4-dichlorophenyl)acetamide methanesulfonic acid salt 2 dissolved in physiological saline was subcutaneously administered to the back of each mouse at a dose of 15 mg/kg, and the survival of the animals thereafter was tested. To the control group, physiological saline was administered in place of Compound 2. The survival rate at 24 hours after administration of LPS (induction of sepsis) was 33.3% in the control group and 60% in the group to which Compound 2 was administered. Thus, it was shown that Compound 2 has a therapeutic effect against sepsis. Compound 2 may be produced in accordance with the method described in U.S. Pat. No. 4,145,435 (1979).

Example 3

Evaluation of Therapeutic Action against Sepsis

ICR mice (bodyweight of 25 g to 35 g when starting the experiments) were raised in a plastic cage under SPF and thermo-hydrostat (22±1° C., 55±5%) conditions under 12-hour light-dark cycle. Foods and water were supplied ad libitum. Lipopolysaccharide (LPS)-induced lethal sepsis which is generally employed as an experimental sepsis model was induced by intrapectoneally administering LPS at a dose of 20 mg/kg. Two hours after administration of LPS when symptoms of sepsis such as diarrhea, worsening of coat of fur and bradykinesia well appeared, (D)Phe-(D)Phe-(D)Nle-(D)Arg-$NH_2$ dissolved in physiological saline was subcutaneously administered to the back of each mouse at a dose of 15 mg/kg, and the survival of the animals thereafter was tested. To the control group, physiological saline was administered in the same manner. The survival rate at 24 hours after administration of LPS (induction of sepsis) was 33.3% in the control group and 66.7% in the group to which (D)Phe-(D)Phe-(D)Nle-(D)Arg-$NH_2$ was administered. Thus, it was shown that (D)Phe-(D)Phe-(D)Nle-(D)Arg-$NH_2$ has a therapeutic effect against sepsis. The above-described peptide compound may be produced in accordance with the methods described in Japanese Laid-open PCT Application No. 11-512075 (1999) or WO99/32510.

Example 4

Evaluation of Therapeutic Action against Sepsis

ICR mice (bodyweight of 25 g to 35 g when starting the experiments) were raised in a plastic cage under SPF and thermo-hydrostat (22±1° C., 55±5%) conditions under 12-hour light-dark cycle. Foods and water were supplied ad libitum. Similar to other examples, experimental sepsis was induced by intraperitoneal administration of lipopolysaccharide (LPS) at a dose of 20 mg/kg. Thereafter, 17-cyclopropylmethyl-3,14β-dihydroxy-4,5α-epoxy-6β-(N-methyl-N'-3-trifluoromethylbenzylureido)morphinan tartaric acid salt 3 dissolved in physiological saline was subcutaneously administered to the back of each mouse at a dose of 3 mg/kg, and the survival of the animals thereafter was tested. To the control group, physiological saline was administered in the same manner. The survival rate at 31 hours after administration of LPS (induction of sepsis) was 30.0% in the control group and 70.0% in the group to which 17-cyclopropylmethyl-3,14β-dihydroxy-4,5α-epoxy-6β-(N-methyl-N'-3-trifluoromethylbenzylureido)morphinan tartaric acid salt 3 was administered. Thus, it was shown that 17-cyclopropylmethyl-3,14β-dihydroxy-4,5α-epoxy-6β-(N-methyl-N'-3-trifluoromethylbenzylureido)morphinan tartaric acid salt 3 has a therapeutic effect against sepsis. Compound 3 may be produced in accordance with the method described in Japanese Patent No. 2525552.

The invention claimed is:

1. A method of treating septic shock comprising administering by injection 0.0001 mg to 1g, or administering 0.005 mg to 10 g in an oral formulation, of an opioid κ receptor agonist morphinan derivative represented by the following Formula (I) or a pharmaceutically acceptable acid addition salt thereof to a patient:

(wherein ⋯ represents a double bond or single bond; $R^1$ is methyl, ethyl, propyl, butyl, isobutyl, cyclopropylmethyl, allyl, benzyl or phenethyl; $R^2$ and $R^3$ independently are hydrogen, hydroxy, acetoxy or methoxy; A represents —$NR^4C(=O)$— or —$NR^4C(=O)O$— or —$NR^4C(=O)NR^4$ (wherein $R^4$ represents $C_1$-$C_5$ linear or branched alkyl and $R^4$s in the formula may be the same or different); B is $C_1$-$C_3$ linear alkylene, —CH=CH—, —C≡C—, —$CH_2$—O—, —$CH_2$—S— or —$CH_2$—NH—; $R^5$ is hydrogen or an organic group having a skeleton selected from those shown below (wherein Q represents O or S; each of said organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy); $R^6$ and $R^7$ cooperatively represent —O—; and $R^8$ represents hydrogen).

2. The method according to claim 1, wherein in said Formula (I), ⋯ is single bond, $R^1$ is cyclopropylmethyl, $R^2$ and $R^3$ are hydroxy, A is —$NR^4C(=O)$—, B is —CH=CH—, $R^5$ is an organic group having a skeleton below:

Q: O.

* * * * *

UNITED STATES PATENT AND TRADEMARK OFFICE
CERTIFICATE OF CORRECTION

PATENT NO. : 7,652,025 B2
APPLICATION NO. : 10/477062
DATED : January 26, 2010
INVENTOR(S) : Suzuki et al.

It is certified that error appears in the above-identified patent and that said Letters Patent is hereby corrected as shown below:

Title page, item (*) Notice: should read as follows: Subject to any disclaimer, the term of this patent is extended or adjusted under 35 U.S.C. 154(b) by 669 days.

In Column 4
At Line 36, Please change "$R_2$" to --$R^2$--.

In Column 7
At line 53, please change "$R_7$" at both occurrences to --$R^7$--; at line 59, please change "$R_5$ and $R_6$" to --$R^5$ and $R^6$--; and at line 61, please change "$R_9$" to --$R^9$--.

In Column 10
At line 45, please change "$NR_4C$" to --$NR^4C$--.

In Column 12
At line 16, please change "R" to --$R^7$--; and at line 22, please change "R" to --$R^4$--.

In Column 14
At line 65, please change "R2" to --$R^2$--.

In Column 21
At line 20, after "7-" please delete "*".

Signed and Sealed this

Twentieth Day of July, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,652,025 B2 | Page 1 of 1 |
| APPLICATION NO. | : 10/477062 | |
| DATED | : January 26, 2010 | |
| INVENTOR(S) | : Suzuki et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 640 days.

Signed and Sealed this

Second Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,652,025 B2 | Page 1 of 1 |
| APPLICATION NO. | : 10/477062 | |
| DATED | : January 26, 2010 | |
| INVENTOR(S) | : Suzuki et al. | |

It is certified that error appears in the above-identified patent and that said Letters Patent is hereby corrected as shown below:

On the Title Page:

The first or sole Notice should read --

Subject to any disclaimer, the term of this patent is extended of adjusted under 35 U.S.C. 154(b) by 668 days.

Signed and Sealed this
Twenty-eighth Day of December, 2010

David J. Kappos
*Director of the United States Patent and Trademark Office*